US006574298B2

United States Patent
Heuscher (10) Patent No.: US 6,574,298 B2
(45) Date of Patent: *Jun. 3, 2003

(54) CONE BEAM SCANNER USING OBLIQUE SURFACE RECONSTRUCTIONS

(75) Inventor: Dominic J. Heuscher, Aurora, OH (US)

(73) Assignee: Koninklijke Philips Electronics, N.V., Eindhoven (NL)

( * ) Notice: Subject to any disclaimer, the term of this patent is extended or adjusted under 35 U.S.C. 154(b) by 0 days.

This patent is subject to a terminal disclaimer.

(21) Appl. No.: 10/054,596

(22) Filed: Jan. 22, 2002

(65) Prior Publication Data

US 2002/0122529 A1 Sep. 5, 2002

Related U.S. Application Data

(63) Continuation of application No. 09/595,858, filed on Jun. 16, 2000, now Pat. No. 6,343,108.
(60) Provisional application No. 60/140,050, filed on Jun. 18, 1999.

(51) Int. Cl.[7] .................................................. A61B 6/03
(52) U.S. Cl. ............................ 378/15; 378/4; 378/901
(58) Field of Search .............................. 378/4, 15, 901

(56) References Cited

U.S. PATENT DOCUMENTS

| 5,170,439 A | 12/1992 | Zeng et al. ..................... 386/6 |
| 5,377,250 A | 12/1994 | Hu ................................ 378/15 |
| 5,396,528 A | 3/1995 | Hu et al. ........................ 378/14 |
| 5,404,293 A | 4/1995 | Weng et al. |
| 5,565,684 A | 10/1996 | Gullberg et al. ........ 250/363.04 |
| 5,592,523 A | 1/1997 | Tuy et al. ...................... 378/19 |
| 5,625,660 A | 4/1997 | Tuy ............................... 378/15 |
| 5,802,134 A | 9/1998 | Larson et al. ................... 378/4 |
| 5,881,122 A | 3/1999 | Crawford et al. ............... 378/4 |
| 5,887,047 A | 3/1999 | Bailey et al. ................... 378/4 |
| 5,909,477 A | 6/1999 | Crawford et al. ............... 378/4 |
| 5,960,056 A | 9/1999 | Lai ................................ 378/4 |
| 6,256,365 B1 * | 7/2001 | Lai .............................. 378/17 |
| 6,256,366 B1 * | 7/2001 | Lai .............................. 378/17 |
| 6,343,108 B1 * | 1/2002 | Heuscher ..................... 378/15 |

OTHER PUBLICATIONS

"Three–Dimensional Helical–Scan Computed Tomography Using Cone–Beam Projections", Kudo, et al. Systems and Computers in Japan, 23 (1992) No. 12.

* cited by examiner

Primary Examiner—David V. Bruce
(74) Attorney, Agent, or Firm—Fay, Sharpe, Fagan, Minnich & McKee, LLP (57) ABSTRACT

Data collected from a cone beam scanner is reconstructed into a volumetric image representation by defining a plurality of oblique surfaces which are reconstructed into a cylinder. An interpolator identifies non-redundant rays of radiation passing through the surfaces. Rays of radiation intersecting a center point of each oblique surface are identified along with rays tangent to surface rings on each surface. Data from the identified non-redundant rays is weighted by a first processor. A second processor convolves the weighted data and passes it to a backprojector which backprojects it into an image memory. The oblique surface reconstruction technique facilitates use of conventional two-dimensional convolution and backprojection techniques that enjoy relative computational simplicity and efficiency as well as three-dimensional reconstruction techniques that use a minimum number of projections. Additionally, the technique facilitates accurate reconstruction of cone beam projections with over ten times the area of current multi-ring scanners.

29 Claims, 11 Drawing Sheets

CONE BEAM SCANNER USING OBLIQUE SURFACE RECONSTRUCTIONS

This application is Continuation Patent Application of pending prior U.S. patent application Ser. No. 09/595,858 filed on Jun. 16, 2000 (now U.S. Pat. No. 6,343,108) which claims the benefit of Provisional application Ser. No. 60/140,050, filed Jun. 18, 1999.

BACKGROUND OF THE INVENTION

The present invention relates to the art of image reconstruction. It finds particular application in conjunction with reconstructing x-ray transmission data from computed tomography (CT) scanners which move a cone-beam or wedge beam of radiation along a helical trajectory, and will be described with particular reference thereto. However, it is to be appreciated that the present invention will also find application in conjunction with the reconstruction of data from CT scanners, nuclear cameras, and other diagnostic scanners that process data representing nonparallel trajectories.

Conventionally, spiral or helical CT scanners include an x-ray source which projects a thin slice or beam of penetrating radiation. The x-ray source is mounted for rotational movement about a subject that is translated along the axis of rotation. An arc or ring of radiation detectors receive radiation which has traversed the subject. Data from the radiation detectors represents a single spiraling slice through the subject. The data from the detectors is reconstructed into a three-dimensional image representation.

Current helical CT scanners with two or three detector rings improve data acquisition speed and permit thin slab scanning. Several 3-D image reconstruction techniques for reconstructing data from helical cone or wedge beam systems have been suggested. For example, commonly assigned U.S. Pat. No. 5,625,660 to Tuy discloses an image reconstruction technique for helical partial cone-beam data in which the data stream is divided into two parts which are processed separately and then recombined. In addition, other similar reconstruction techniques process a single data stream. These three-dimensional reconstruction techniques generally involve increased computational load and complexity. This is due to the fact that these reconstruction techniques perform "true 3D reconstruction," involving a 3D backprojection of convolved projections.

In contrast, current 2D helical reconstruction techniques enjoy decreased computational load and simplicity. However, current 2D helical reconstruction techniques limit the number of rings or cone angle over which accurate reconstructions can be obtained. An additional difficulty with reconstruction of spiral cone or wedge beam data is the elimination of redundant rays of data.

The present invention contemplates a new and improved image reconstruction technique which overcomes the above-referenced problems and others.

SUMMARY OF THE INVENTION

In accordance with one aspect of the present invention, a method of volumetric image reconstruction includes collecting partial cone beam data in two-dimensional arrays at a plurality of sampling positions, where the collected data corresponds to rays of radiation which diverge in two dimensions from a common vertex as the vertex travels along a continuous path. A plurality of two-dimensional oblique surfaces are defined throughout a region of interest and rays of radiation which pass through the plurality of oblique surfaces are defined. The data from the identified rays is reconstructed into a reconstruction cylinder having an axis along a z-direction. A volume data set is generated from the reconstructed oblique surface data.

In accordance with another aspect of the present invention, a method of diagnostic imaging includes generating penetrating radiation and the receiving the penetrating radiation with two-dimensional radiation detectors along a plurality of divergent rays, where the rays are focused at a common origin vertex and diverge in two dimensions. The vertex is rotated along at least an arc segment of a helical path. The radiation detectors are sampled at a plurality of angular increments along the helical arc segment to generate a plurality of two-dimensional projection views, where each view includes a two-dimensional array of data values and each data value corresponds to one of the divergent rays. A first and last oblique surface are defined, where the first and last oblique surfaces are formed by the intersection of a cone beam of penetrating radiation and the region of interest. A plurality of additional oblique surfaces are defined, where the plurality of oblique surfaces are at least one of rotated and translated with respect to the first oblique surface. Projection views corresponding to each oblique surface are weighed and a two-dimensional convolution of the projection view data is computed. The convolved projection data corresponding to each oblique surface is two-dimensionally backprojected into a volumetric image memory.

In accordance with another aspect of the present invention, a method of selecting non-redundant rays of penetrating radiation during a computed tomography scan is provided where the non-redundant rays from a plurality of oblique surfaces for two-dimensional reconstruction into a volumetric image representation. The method includes at each angular orientation about an examination region, selecting detected rays of penetrating radiation that intersect a geometric center point of each oblique surface. The method further comprises interatively identifying rays of penetrating radiation which are tangent to surface rings extending outward from the geometric center point of each oblique surface.

In accordance with a more limited aspect of the present invention, the method includes where penetrating radiation data does not exist, interpolating closest adjacent rays tangent to the oblique surface rings between the center point and an outer radius of the region of interest.

In accordance with another aspect of the present invention, a computed tomography scanner includes a first gantry which defines an examination region and a rotating gantry mounted to the first gantry for rotation about the examination region. A source of penetrating radiation is arranged on the rotating gantry for rotation therewith. The source of penetrating radiation emit a cone-shaped beam of radiation that passes through the examination region as the rotating gantry rotates. A subject support holds a subject being examined at least partially within the examination region, wherein at least one of the first gantry and the subject support is translated such that the subject passes through the examination region while the rotating gantry is rotated and the source of penetrating radiation follows a helical path relative to the subject. A two dimensional array of radiation detectors is arranged to receive the radiation emitted from the source of penetrating radiation after it has traversed the examination region. A reconstruction processor reconstructs images of the subject from data collected by the two-dimensional array of radiation detectors. The reconstruction processor includes a control processor which defines a plurality of oblique surfaces, where the oblique surfaces are defined by the intersection of the cone-shaped beam of radiation and a portion of the subject, and an interpolator which identifies non-redundant rays of penetrating radiation that pass through the oblique surfaces. A first data processor weights the data corresponding to the identified non-redundant rays and a second data processor receives data from the first data processor and performs a two-dimensional convolution on the data. A backprojector receives the data from the second data processor and two-dimensionally backprojects it into an image memory. The CT scanner further includes a human-viewable display which accessed an image memory to display to display reconstructed images of the subject.

One advantage of the present invention is increased efficiency in both the scan and reconstruction process.

Another advantage of the present invention is that it provides accurate reconstruction for larger area cone beam projections.

Another advantage of the present invention is that it enjoys greater computational simplicity.

Yet another advantage of the present invention resides in the ability to achieve a three-dimensional volumetric reconstruction using conventional two-dimensional reconstruction techniques.

Other benefits and advantages of the present invention will become apparent to those skilled in the art upon a reading and understanding of the preferred embodiments.

BRIEF DESCRIPTION OF THE DRAWINGS

The invention may take form in various components and arrangements of components, and in various steps and arrangements of steps. The drawings are only for purposes of illustrating preferred embodiments and are not to be construed as limiting the invention.

DETAILED DESCRIPTION OF THE PREFERRED EMBODIMENTS

Figure 1:
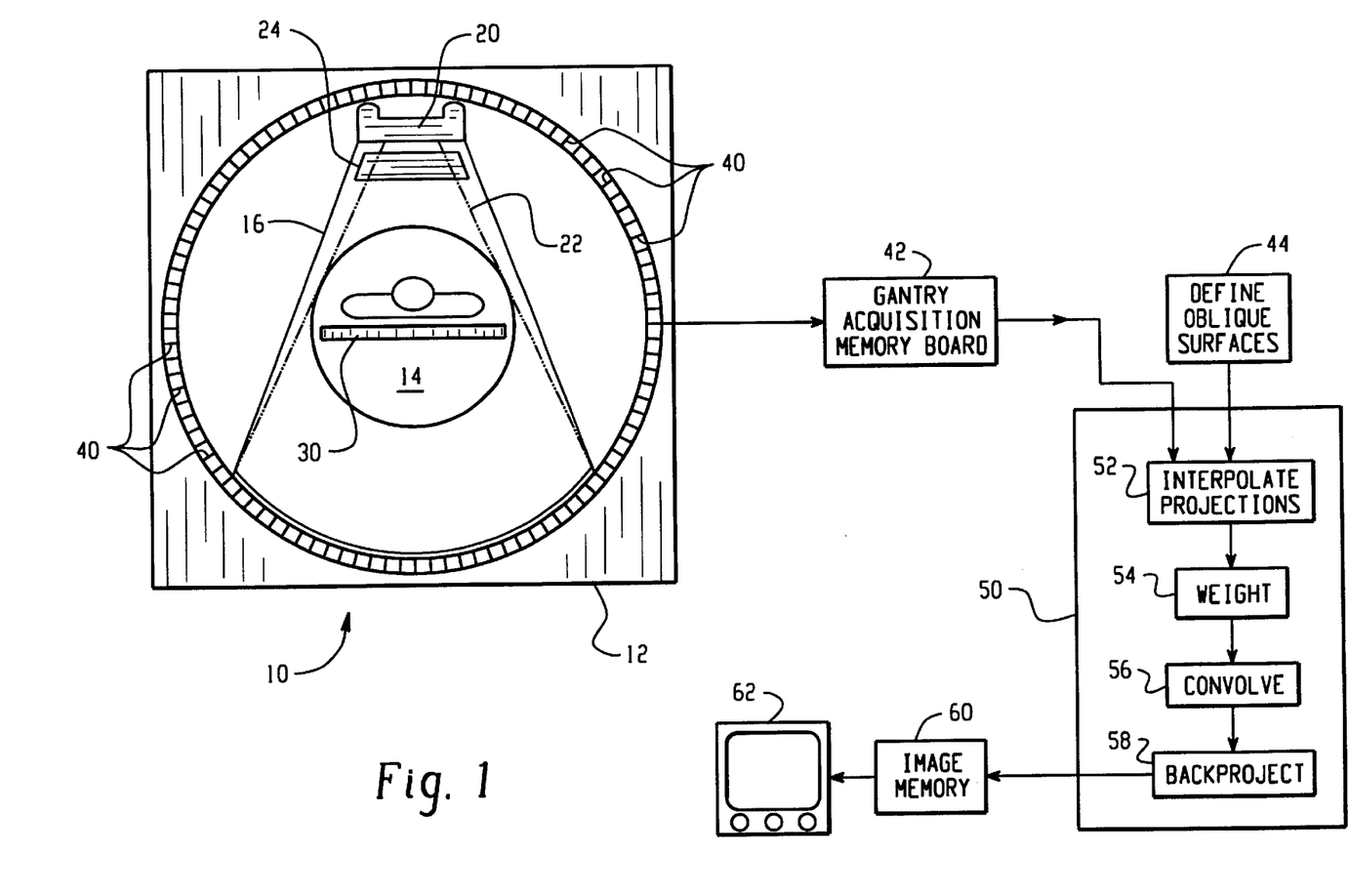
FIG. 1 is a diagrammatic illustration of a computerized tomographic (CT) diagnostic system in accordance with aspects of the present invention.

With reference to FIG. 1, a computed tomography (CT) scanner 10 includes a stationary gantry 12 which defines an examination region 14. A rotating gantry 16 is mounted on the stationary gantry 12 for rotation about the examination region 14. A source of penetrating radiation 20, such as an x-ray tube, is arranged on the rotating gantry 16 for rotation therewith. The source of penetrating radiation is collimated to produce a cone-shaped beam of radiation 22 that passes through the examination region 14 as the rotating gantry 16 rotates. A collimator and shutter assembly 24 shapes the beam of radiation 22 and selectively gates the beam 22 on and off. Alternately, the radiation beam 22 is gated on and off electronically at the source 20.

A subject support 30, such as a couch or the like, suspends or otherwise holds a subject being examined or imaged at least partially within the examination region 14. Moreover, as the rotating gantry 16 rotates, the support 30, and consequently the subject thereon, are translated along a central horizontal axis of the examination region 14. In this manner, the source 20 follows a helical path relative to the subject. Optionally, in an alternative embodiment, the support 30 remains stationary while the "stationary gantry" 12 is translated or otherwise moved relative to the subject such that the source 20 follows a helical path relative thereto.

In the illustrated fourth generation CT scanner, a plurality of rings of radiation detectors 40 are mounted peripherally around the examination region 14 on the stationary gantry 12. Alternately, in a preferred embodiment, a third generation CT scanner is employed with a two-dimensional array of the radiation detectors 40 mounted on the rotating gantry 16 on a side of the examination region 14 opposite the source 20 such that they span the area defined by the cone-shaped beam of radiation 22. Regardless of the configuration, the radiation detectors 40 are arranged such that a two-dimensional array thereof receive the radiation emitted from the source 20 after it has traversed the examination region 14.

In a source cone geometry, an array of detectors which span the radiation 22 emanating from the source 20 are sampled concurrently at short time intervals as the source 20 rotates behind the examination region 14 to generate a source view. In a detector cone geometry, each detector is sampled a multiplicity of times in each of a plurality of revolutions as the source 20 rotates behind the examination region 14 to generate a detector view. The path between the source 20 and each of the radiation detectors 40 is denoted as a ray.

The radiation detectors 40 convert the detected radiation into electronic data. That is to say, each of the radiation detectors produces an output signal which is proportional to the intensity of received radiation. Optionally, a reference detector may detect radiation which has not traversed the examination region 14. A difference between the magnitude of radiation received by the reference detector and each active radiation detector 40 provides an indication of the amount of radiation attenuation or absorption along a corresponding ray of sampled radiation.

In detector view geometry, each view or two-dimensional array of data represents a cone of rays having its vertex at one of the radiation detectors 40 collected over one or more short periods of time as the source 20 rotates behind the examination region 14 from the detectors. In source view geometry collected by a concurrent sampling of detectors, each view has a complete two-dimensional array of data representing a cone of rays having a vertex at the source 20 and a ray from the source to every detector. In a source view, the resolution is limited by the detector size and the number of views is limited by the sampling rate. In a detector view, the resolution is limited by the sampling rate and the number of views is determined by the detector size.

A gantry acquisition memory board 42 receives sampled data from the radiation detectors 40 and gantry geometry parameters, such as helix pitch. The gantry acquisition memory board 42 organizes the data into a selected one of a detector cone geometry and a source cone geometry and performs a ripple filtering operation before passing the data to a control processor 44 which defines a plurality of oblique surfaces, the operation of which is described more fully below. A reconstruction processor 50 processes the collected and manipulated data from the gantry acquisition memory board 42 and control processor 44 and ultimately two-dimensionally backprojects it into an image memory 60 for access and display on a human-viewable display 62, such as a video monitor.

Figure 2A:
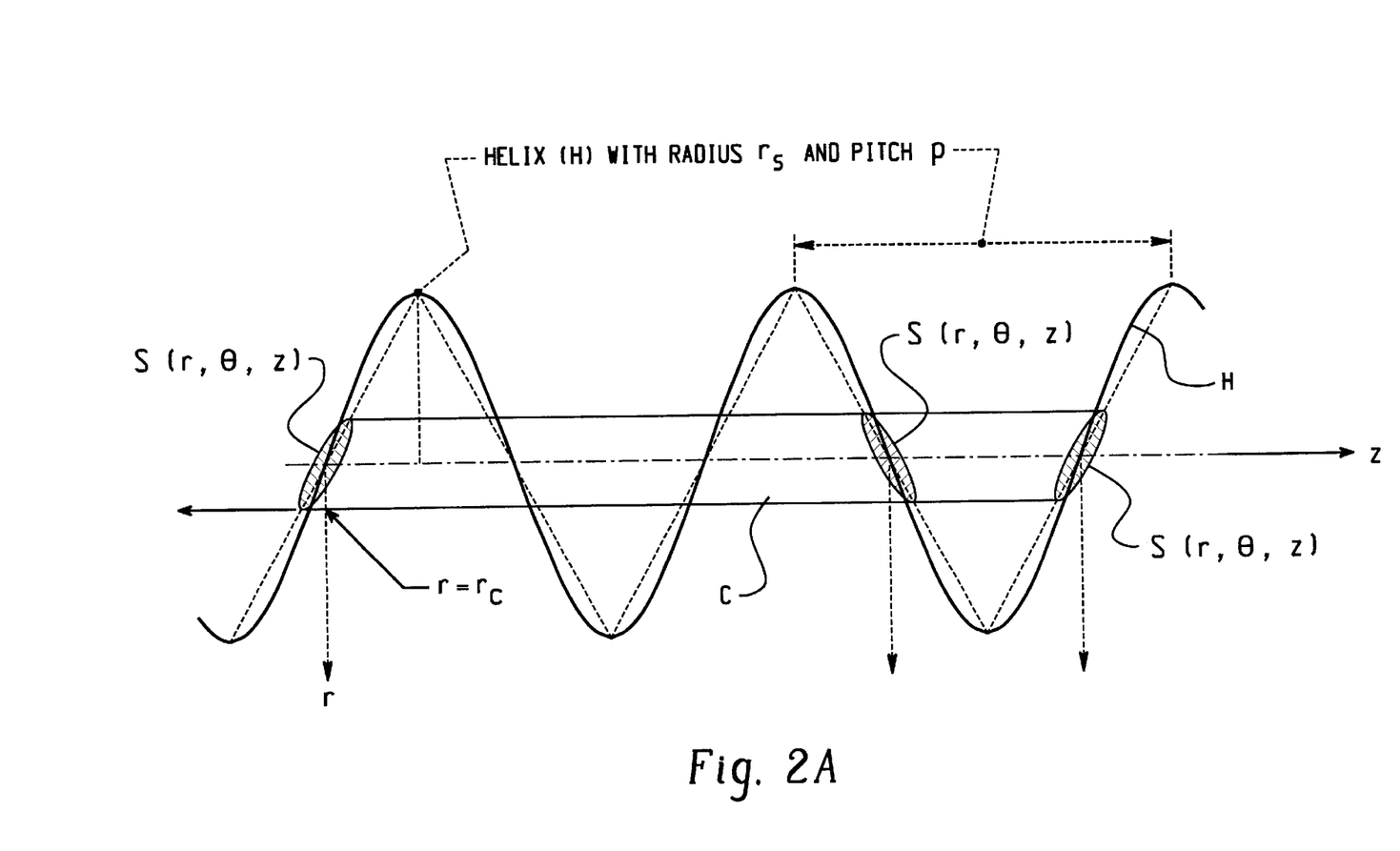
FIG. 2A is an expanded sagittal view of a reconstruction cylinder having a radius $r_c$ and a length $z_c$ in accordance with the present invention.
Figure 2B:
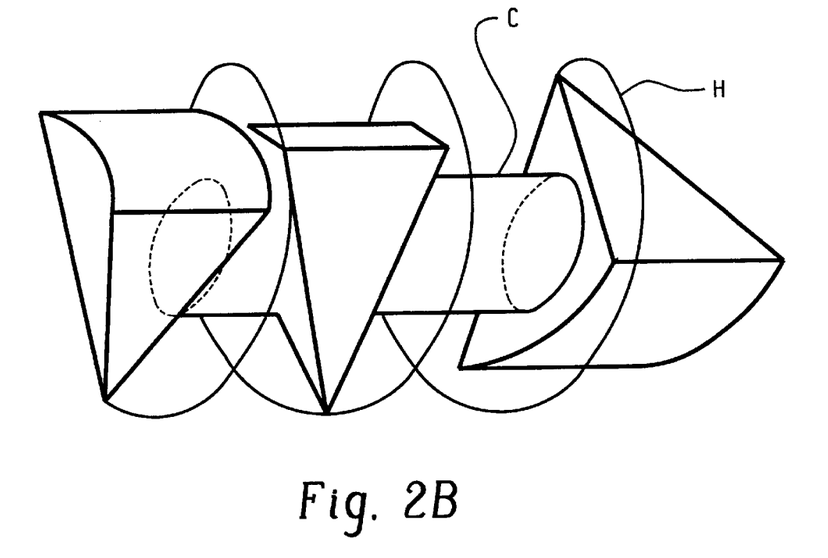
FIG. 2B is an expanded three-dimensional view of a reconstruction cylinder of FIG. 2A with a cone beam of radiation superimposed at three locations along the z-direction.

More particularly, the reconstruction processor 50 includes an interpolator 52 which interpolates oblique surface projections based on a defined first oblique surface, $S_1(r, \theta, z)$. As is described more fully below, a plurality of these oblique surfaces, each rotated and translated with respect to the first oblique surface, make up the full volume of a reconstruction cylinder C. FIGS. 2A and 2B show a sagittal view and a corresponding three-dimensional view of the reconstruction cylinder C. The reconstruction cylinder C represents the volume of interest or scanned volume for the particular diagnostic study being performed. In other words, the portion of the subject which is being examined lies within the boundaries of the reconstruction cylinder. As shown in FIG. 2A, the reconstruction cylinder has a radius $r_c$ and a length $z_c$.

Figure 2C:
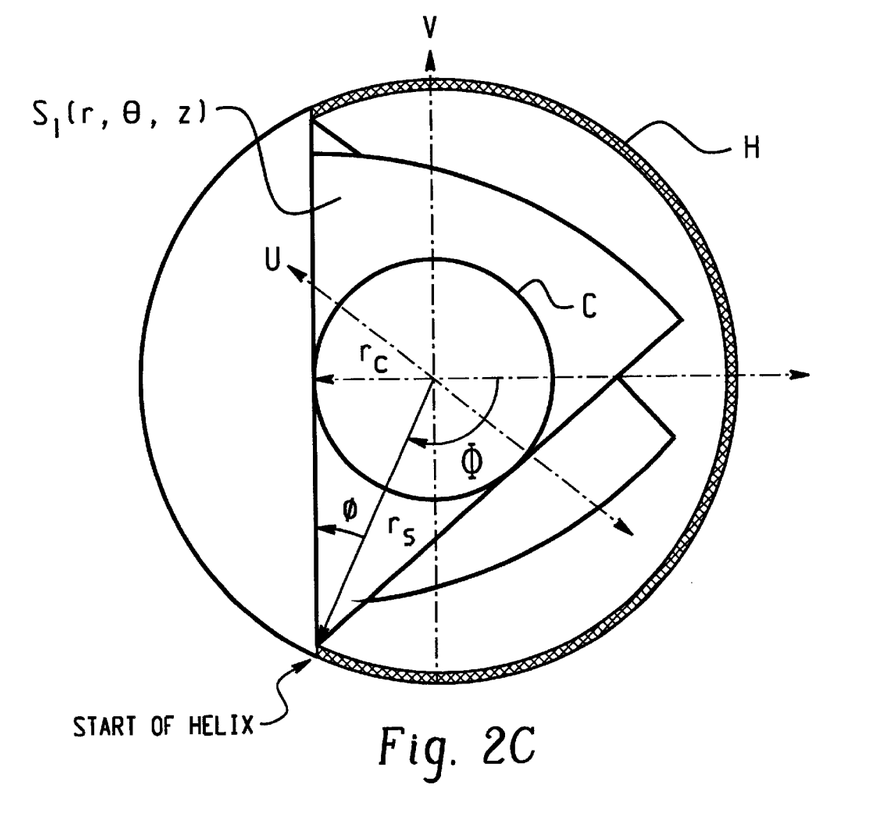
FIG. 2C is an axial view of the reconstruction cylinder shown in FIGS. 2A and 2B.

As described above, the radiation source 20 moves along a helical trajectory H with respect to the subject disposed within the examination region 14. The helix H with radius $r_s$ and pitch p extends from a start angle of $\Phi = -\phi - \pi/2$ to $\Phi = 2\pi z_c/p + \phi + \pi/2$ for a total angle of $2\pi z_c/p + 2\phi + \pi$, where $\phi = \sin^{-1}(r_c/r_s)$ is the additional rotation angle beyond $\pi$ for completely reconstructing the oblique surface $S_1(r, \theta, z)$ and is shown in the axial view of the reconstruction cylinder (FIG. 2C). The minimum rotation angle to reconstruct each oblique surface is $2\phi + \pi$ or 180° plus the cone angle or fan angle of the radiation source, where the fan angle is defined by the diameter of the reconstruction cylinder C. While the present invention is described in terms of a source moving along helical trajectory, it is to be appreciated that it is applicable to scanners employing other source trajectories.

Figure 2D:
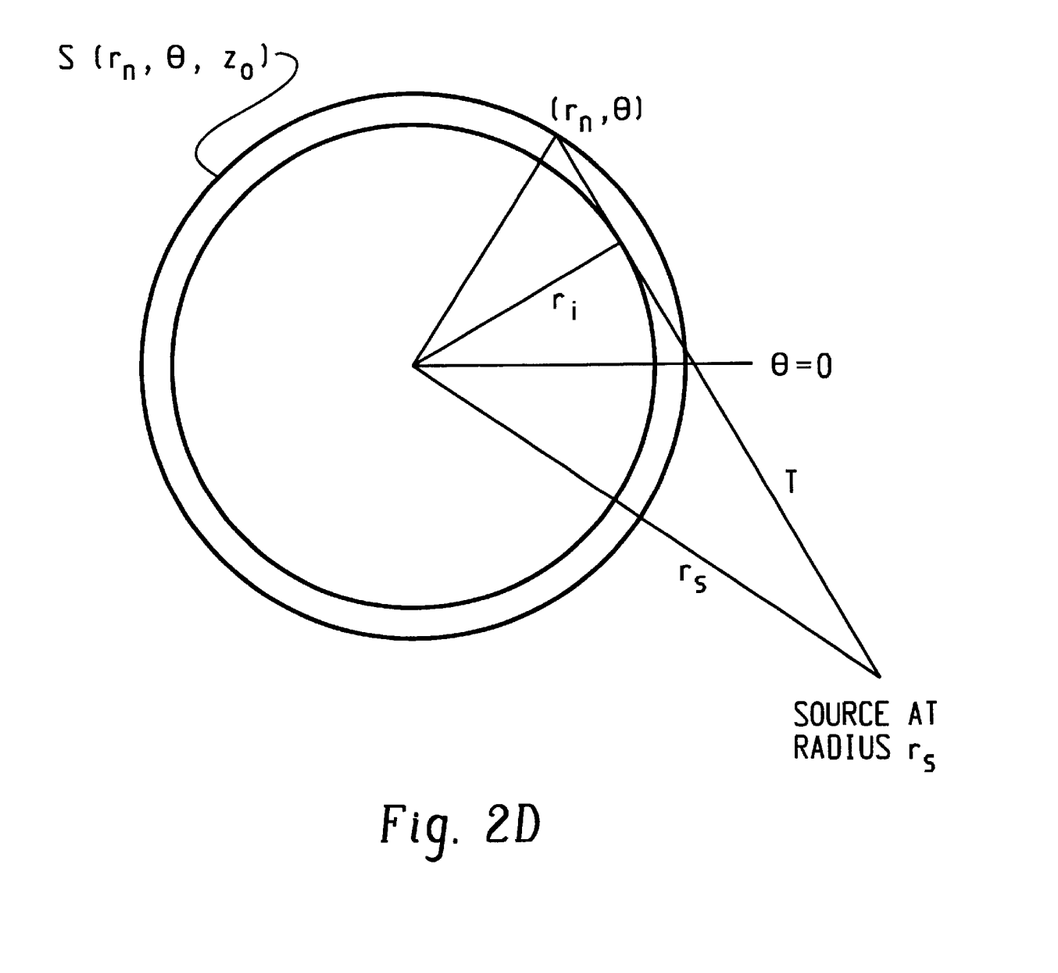
FIG. 2D is a diagrammatic illustration of the oblique surface derivation in accordance with the present invention.

With reference to FIG. 2D and continuing reference to FIG. 1, once the oblique surfaces are defined 44 based on control parameters, such as helical pitch and radius, the interpolator 52 identifies non-redundant rays of radiation which pass through each oblique surface. The oblique two-dimensional surface $S(r, \theta, z)$ is defined by iteratively aligning the detected rays of radiation by interpolation of the cone beam projections to equal the mean (weighted) z-axis position of all rays tangent to the cylinder $(r, \theta)$, extending to the outer radius $r_c$ of the reconstruction cylinder C. This iterative process is expressed as:

$$S(r_n, \theta, z_0) = \frac{\sum_{i=0\ldots n-1} W(\theta_T) Z_T(r_i, r_n, \theta, z_0) \Delta\theta(r_i, r_n)}{\sum_{i=0\ldots n-1} \Delta\theta(r_i, r_n)}$$

for $r_n = 0 \ldots r_c$, where:
- $W(\theta_T) = 180°$ plus fan weighting for rays (T) tangent to the cylinder of radius $r_i$,
- $Z_T(r_i, r_n, \theta, z_0)$ = z-axis location at $(r_n, \theta)$ of rays (T) tangent to the cylinder of radius $r_i$, and
- $\Delta\theta(r_i, r_n)$ = angular increment between rays intersection at $(r_n, \theta)$.

Figure 3:
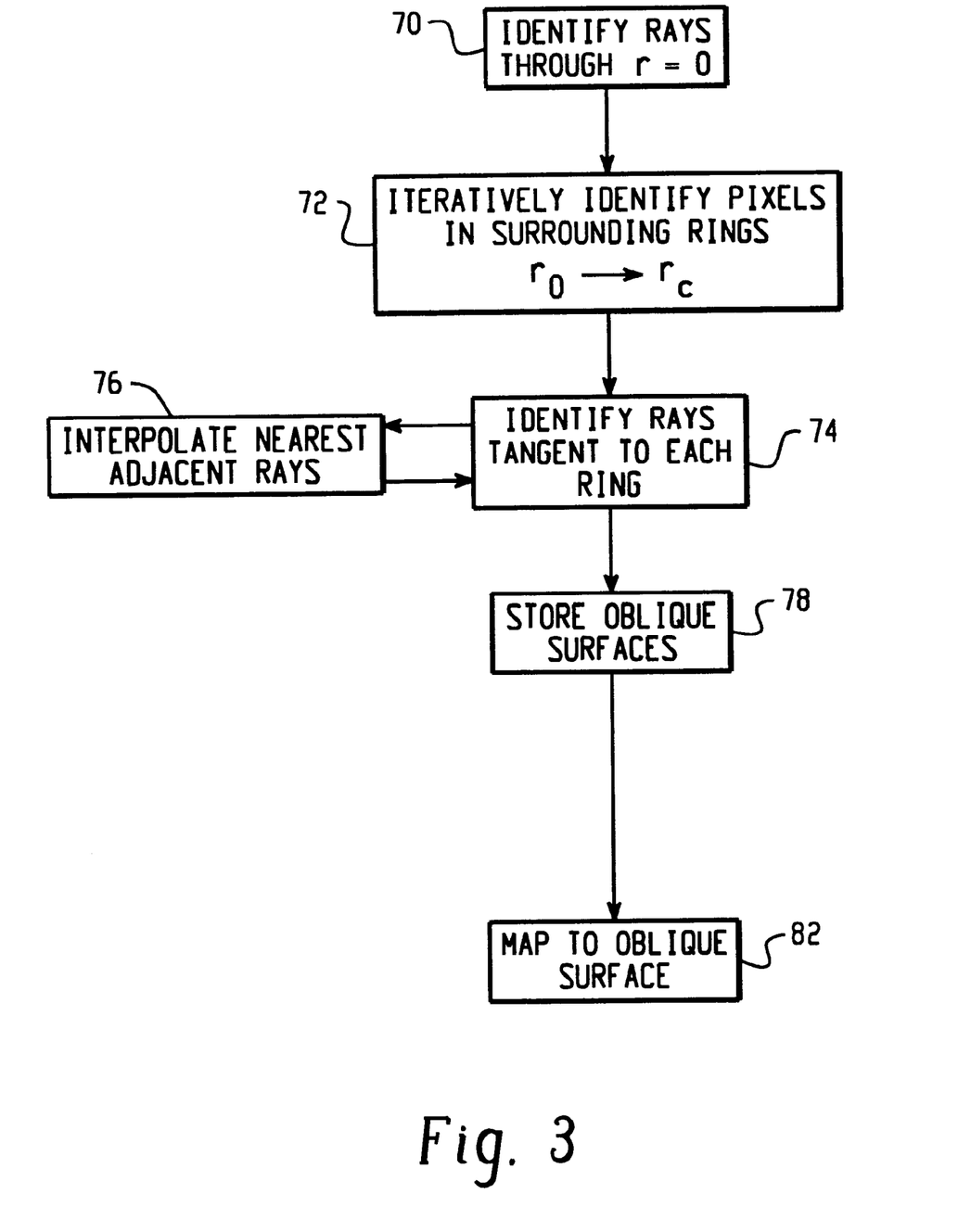
FIG. 3 is a flow chart illustrating the interpolation method in accordance with the present invention; and, FIGS. 4A–4F are flow charts illustrating alternate embodiments of the oblique surface reconstruction method in accordance with the present invention.

With reference to FIG. 3, the interpolator 52 identifies all rays of radiation that intersect a center point $(0, \theta, z)$ of each oblique surface 70. The interpolator 52 then iteratively identifies pixels at least one pixel out from the center point of each oblique surface 72, where these pixels form a plurality of surface rings which extend from the center point to the outer radius $r_c$ of the reconstruction cylinder C, as is described mathematically above. The interpolator then iteratively identifies rays of radiation that are tangent to each of the plurality of surface rings 74, interpolating closest adjacent rays 76, where necessary.

This process defines a plurality of oblique surfaces throughout the reconstruction cylinder C, which are stored 78, along with the corresponding ray positions, in an intermediate memory as $S(x,y,z(x,y))$. Further, the iterative process results in a plurality of oblique surfaces with minimum dispersion, i.e. minimal z-axis deviations of the projected rays from each surface $S(r, \theta, z)$. Each of the plurality of oblique surfaces is rotated and translated with respect to the first oblique surface $S_1(r, \theta, z)$ to make up the full volume of the reconstruction cylinder C, given by: $S(r, \theta, z) = S(r, \theta + 2\pi(z - z_0)/p, z_0) + z - z_0$. Otherwise, the oblique surfaces will change along the source trajectory, with each surface definition requiring a source path segment of at least 180° plus the fan angle.

In order to adequately sample the volume, the spacing between the reconstructed surfaces along the z-axis is selected to be no more than one-half the effective z-axis resolution ($\leq \Delta z/2$). The maximum dispersion occurs at the radius $r_c$. A "dispersion factor" $\rho$ is defined as:

(maximum z-axis deviation from the surface at radius $r_c$)/$\Delta z$, where $\Delta z$ is the effective z-axis resolution. It should be appreciated that maximum dispersion tolerances are of lesser importance in embodiments where three-dimensional reconstruction algorithms are employed because of the far greater accuracy present in the three-dimensional embodiments.

The interpolated rays defining each reconstructed surface are weighted $W(\theta)$ by an appropriately smooth weighting function, such that the weights of all opposing rays sum to unity, with all other rays having a weighting factor of one. That is, rays which travel substantially the same trajectory in opposite directions are replaced by an average of the two. Because the dispersion factor increases with helical pitch, a maximum value of the dispersion factor can be used to define the maximum pitch of the helix that accurately reconstructs the cylinder of radius $r_c$.

Once the end surfaces of the reconstruction cylinder are defined, the leading and trailing collimation of the cone beam are also defined. All non-zero weighted projections, required to reconstruct each oblique surface, map to a detector surface 82 that encompasses the reconstruction cylinder C and extends along the z-axis over a distance (projected at r=0) of approximately p/2. The detector surface is slightly oblique to the normal of the z-axis, depending on the helical pitch p.

It should be appreciated that a thin slab, such as 3–6 substantially parallel rows, may be defined instead of a two-dimensional oblique surface. In this embodiment, once the rays or radiation passing through a surface are identified, the adjoining rays, fore and aft, in the appropriate direction are considered as passing through two parallel surfaces of a slab.

Referring again to FIG. 1, a first data processor 54 weights the data from the identified rays passing through each oblique surface. In one embodiment, conventional plus-region weighting along $Z(\theta)$ is applied based on 180° oblique surface projections and end projections. In addition, cone beam angle weighting is optionally applied to account for angular distribution of backprojected rays. A second data processor 56 receives the data from the first data processor 54 and performs a conventional two-dimensional convolution on the data. A backprojector 58 receives the convolved data from the second data processor 56 and two-dimensionally backprojects the oblique surface projections over 180° after combining complimentary views. In another embodiment, the backprojector 58, performs a V-weighted backprojection of oblique surface projections over the full 180° plus fan. In another embodiment, a three-dimensional backprojection is performed for sets of projections with the Z interpolation of the projections corresponding to a linear position along the oblique surface image matrix.

It should be appreciated that the interpolated projections corresponding to each surface may be interpolated into either fan-beam or parallel-beam projections, depending on the density of views collected in one revolution of the helix.

Once the oblique surfaces are reconstructed, the reconstruction cylinder C may be re-sampled onto an orthogonal matrix $C(x,y,z)$ by interpolating the reconstructed surfaces $S(x,y,z)$ for each $(x,y)$ value along the z-direction. In other words $C(x,y,z)$ is mapped from the reconstructed surface matrix $S(x,y,z(x,y))$.

It should be appreciated that tradeoffs may be made between the dispersion factor and helical pitch. For example, for the same dispersion at radius $r_c=125$ mm versus $r_c=250$ mm, scans with almost twice the helical pitch may be used.

Figure 4A:
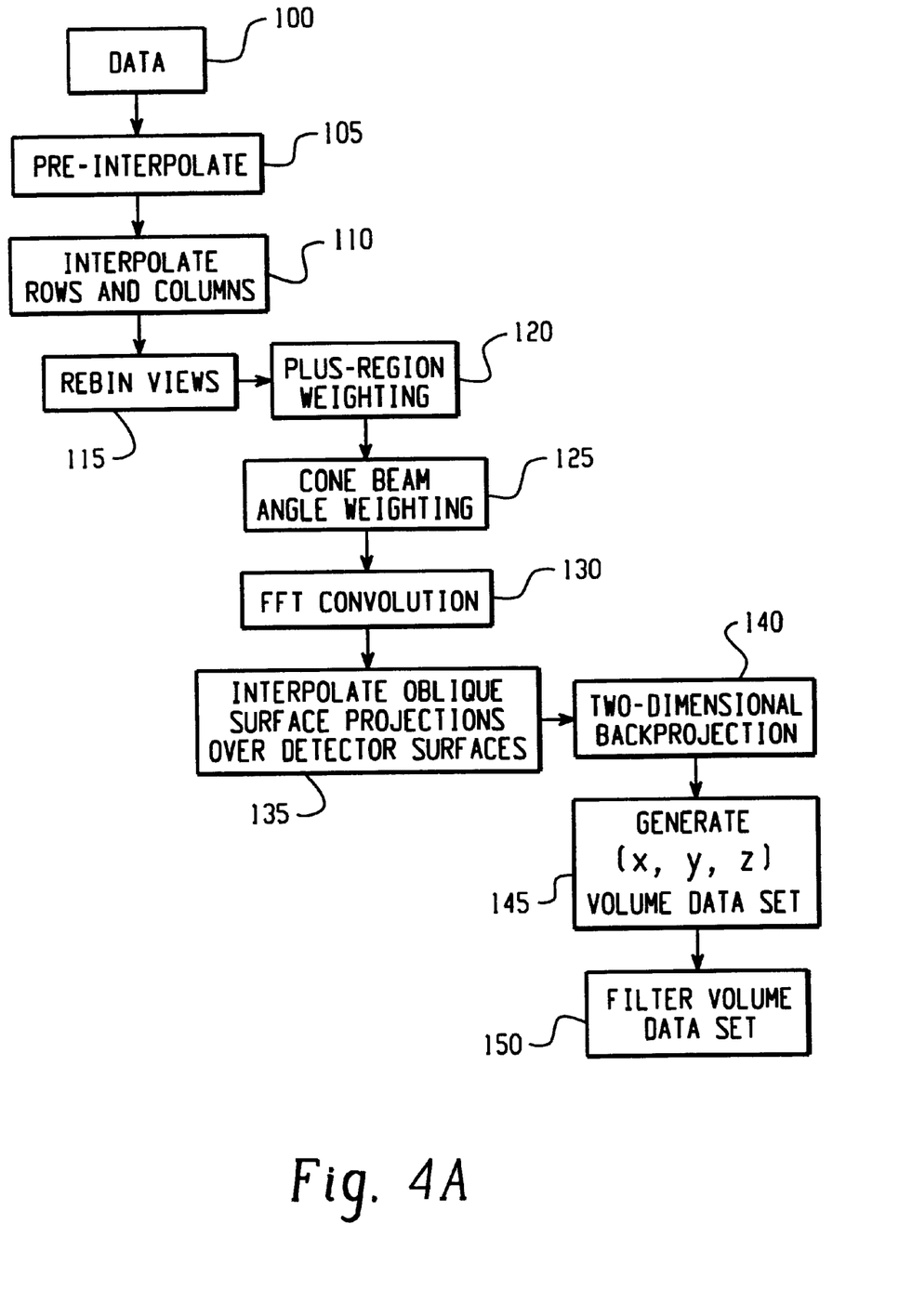

With reference to FIGS. 4A–4F, six alternate embodiments for the reconstruction of oblique surfaces are provided. FIG. 4A is preferred for cone beam scans where the cone angle is sufficiently narrow to permit accurate reconstruction using simple 2D backprojection of oblique surfaces. More particularly, data is collected 100 in the native sampling geometry, such as flat, source arc, or scan center arc. Columns and rows are pre-interpolated 105 or up-sampled by a factor of two using high-order interpolation. Optionally, the first and last rows are duplicated, if necessary. Alternately, for embodiments in which the number of rows is small, the 180° data points from the first row are used to interpolate the points at the end of the last row. The row and column elements are interpolated 110 to generate equiangular data which is orthogonal to the z-axis with the rows and partial rows equally spaced along the z-axis. The views are rebinned 115 in both the azimuthal and radial directions.

Following rebinning 115, a plus-region weighting algorithm is applied 120 along $Z(\theta)$ based on 180° oblique surface projections and end projections. In order to account for the angular distribution of backprojected rays, a cone beam angle weighting algorithm 125 is applied. Elements in each row have the same cosine weight value because the rows are equally distributed along the z-axis. After the projections along rows are completed, a FFT convolution 130 is performed on all of the rows. Following the convolution, the oblique surface projections are interpolated 135 over each detector surface into oblique surface projection rows and columns.

The oblique surface projections are two-dimensionally backprojected 140 over 180° after combining complimentary views. A rectangular $(x,y,z)$ volumetric data set is generated 145 by interpolating the oblique surface matrices along the z-direction. It should be appreciated that the sequence of reconstructions along the z-axis is separated by no more that the half-width of a single radiation detector. The resulting volumetric data set is filtered 150 along the z-direction to define the effective z-axis resolution.

Figure 4B:
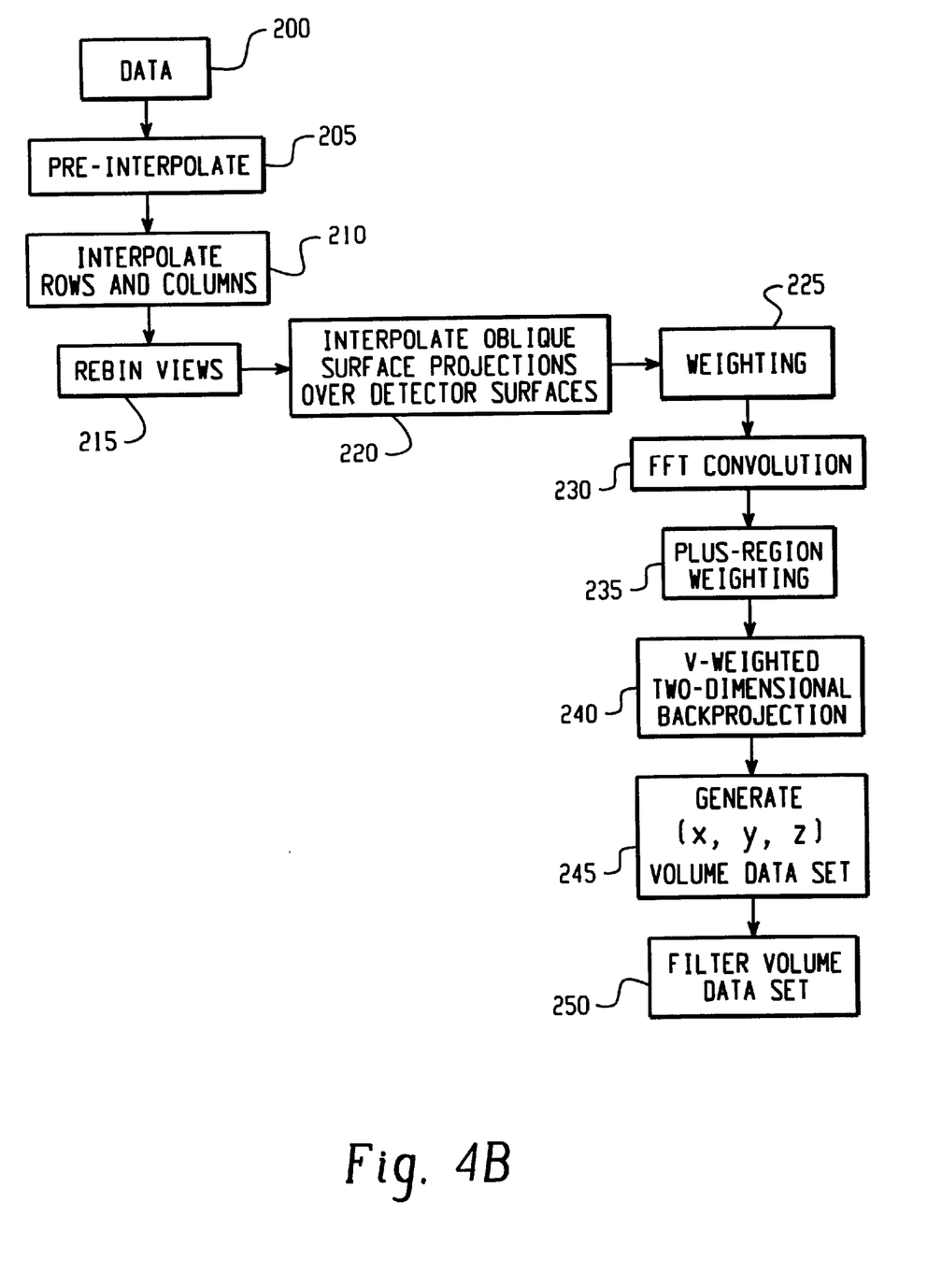

FIG. 4B provides an alternate embodiment which provides tradeoffs in image quality and requires the addition of linear depth weighting during the two-dimensional backprojection. More particularly, data is collected 200 in the native sampling geometry, such as flat, source arc, or scan center arc. Columns and rows are pre-interpolated 205 or up-sampled by a factor of two using high-order interpolation. Optionally, the first and last rows are duplicated, if necessary. Alternately, for embodiments in which the number of rows is small, the 180° data points from the first row are used to interpolate the points at the end of the last row. The row and column elements are interpolated 210 to generate equiangular data which is orthogonal to the z-axis with the rows and partial rows equally spaced along the z-axis. The views are rebinned 215 in both the azimuthal and radial directions.

Following rebinning 215, the oblique surface projections are interpolated 220 over the extent of the detector surface, where the skew is tangent to two points along the end rows. An oblique surface projection weighting 225 is applied proportional to the inverse distance between interpolated samples along U. It should be appreciated that U and V are projection space directions, as illustrated in FIG. 2C. After the projections along rows are completed, a FFT convolution 230 is performed on all of the rows. Following the convolution, a plus-region weighting algorithm is applied 235 along $Z(\theta)$ based on 180° oblique surface projections and end projections.

The oblique surface projections are V-weighted, two-dimensionally backprojected 240 over the full 180° plus angle. The V-weighting is applied using a linear weighted set of values between $W_{maxv}$ (U) and $W_{minv}$ (U). The V-weighting compensates for convolving dispersed rays in each oblique surface projection. A rectangular $(x,y,z)$ volumetric data set is generated 245 by interpolating the oblique surface matrices along the z-direction. It should be appreciated that the sequence of reconstructions along the z-axis is separated by no more that the half-width of a single radiation detector. The resulting volumetric data set is filtered 250 along the z-direction to define the effective z-axis resolution.

Figure 4C:
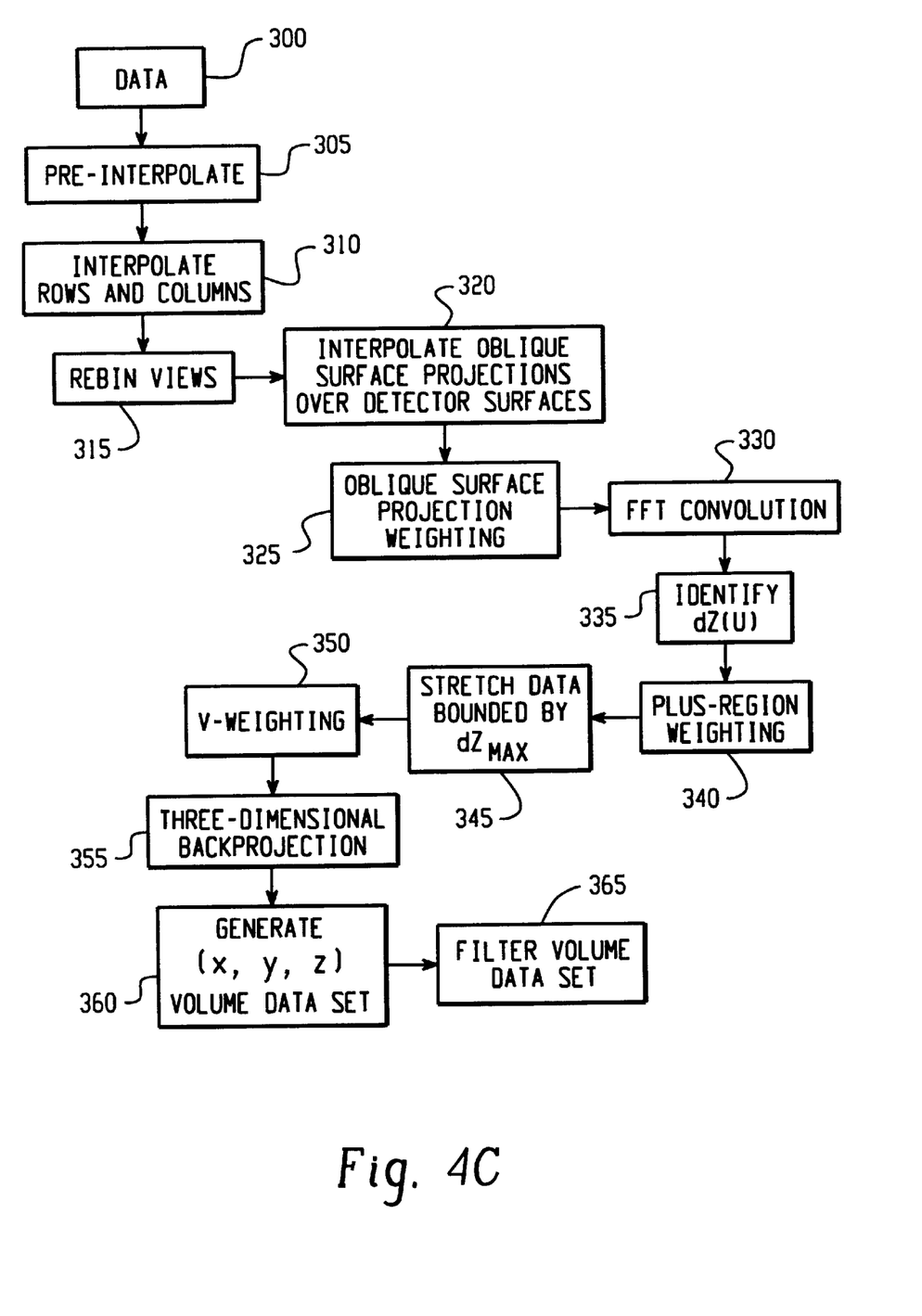

FIG. 4C illustrates an alternate embodiment which is particularly accurate for large cone angles. More particularly, data is collected 300 in the native sampling geometry, such as flat, source arc, or scan center arc. Columns and rows are pre-interpolated 305 or up-sampled by a factor of two using high-order interpolation. Optionally, the first and last rows are duplicated, if necessary. Alternately, for embodiments in which the number of rows is small, the 180° data points from the first row are used to interpolate the points at the end of the last row. The row and column elements are interpolated 310 to generate equiangular data which is orthogonal to the z-axis with the rows and partial rows equally spaced along the z-axis. The views are rebinned 315 in both the azimuthal and radial directions.

Following rebinning 315, the oblique surface projections are interpolated 320 over the extent of the detector surface, where the skew is tangent to two points along the end rows. An oblique surface projection weighting 325 is applied proportional to the inverse distance between interpolated samples along U. After the projections along rows are completed, a FFT convolution 330 is performed on all of the rows. Following the convolution, $dZ(U)$ required to backproject onto a surface at $z=z_0$ is identified 335 around each oblique surface. A plus-region weighting is applied 340 for all samples in a given region within each view. The samples are interpolated to stretch the data 345 along U bounded by dZ(U) to projections bounded by $dZ_{max}$. V-weighting is applied 350 using a linear weighted set of values between $W_{maxv}(U)$ and $W_{minv}(U)$ to the region bounded by $dZ_{max}$. The V-weighting compensates for convolving dispersed rays in each oblique surface projection. A three-dimensional backprojection is applied 355 to the sets of projections with the Z interpolation of the projections corresponding to a linear position in V along the oblique surface image matrix. A rectangular (x,y,z) volumetric data set is generated 360 by interpolating the oblique surface matrices along the z-direction. It should be appreciated that the sequence of reconstructions along the z-axis is separated by no more that the half-width of a single radiation detector. The resulting volumetric data set is filtered 365 along the z-direction to define the effective z-axis resolution.

Figure 4D:
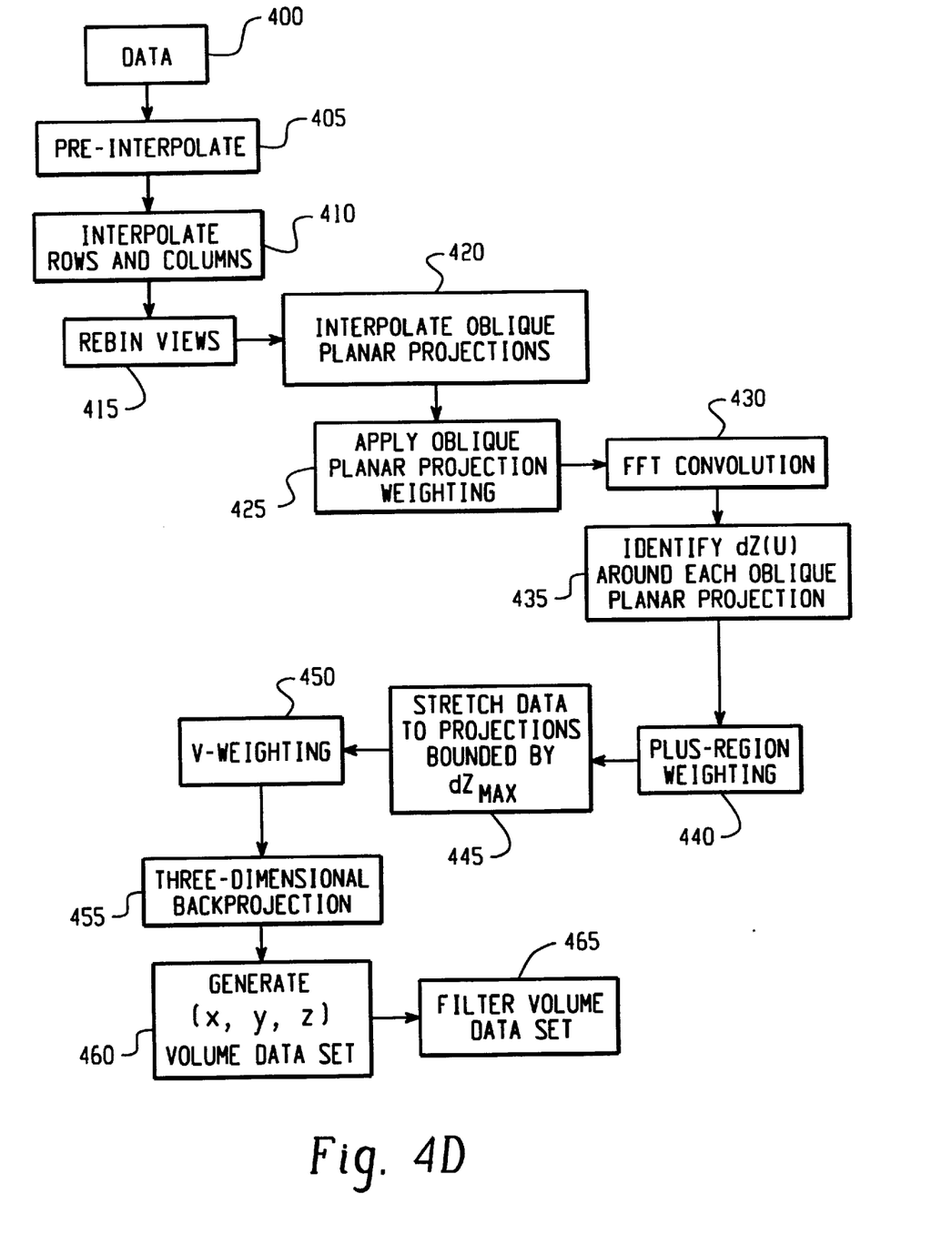

FIG. 4D illustrates an alternate embodiment which is analogous to the embodiment illustrated in FIG. 4C where the oblique surfaces are defined as planar surfaces. More particularly, data is collected 400 in the native sampling geometry, such as flat, source arc, or scan center arc. Columns and rows are pre-interpolated 405 or up-sampled by a factor of two using high-order interpolation. optionally, the first and last rows are duplicated, if necessary. Alternately, for embodiments in which the number of rows is small, the 180° data points from the first row are used to interpolate the points at the end of the last row. The row and column elements are interpolated 410 to generate equiangular data which is orthogonal to the z-axis with the rows and partial rows equally spaced along the z-axis. The views are rebinned 415 in both the azimuthal and radial directions.

Following rebinning 415, the oblique planar projections are interpolated 420 over the extent of the detector surface, where the skew is tangent to two points along the end rows. An oblique planar projection weighting 425 is applied proportional to the inverse distance between interpolated samples along U. It is to be appreciated that for oblique planar projections, the oblique planar projection weighting 425 corresponds to a constant value for each projection. After the projections along rows are completed, a FFT convolution 430 is performed on all of the rows.

Following the convolution, the dZ(U) required to backproject onto the plane at $z=z_0$ is identified 435 around each oblique planar projection. A plus-region weighting is applied 440 for all samples in a given region within each view. The samples are interpolated to stretch the data 445 along U bounded by dZ(U) to projections bounded by $dZ_{max}$. V-weighting is applied 450 using a linear weighted set of values between $W_{maxv}(U)$ and $W_{minv}(U)$ to the region bounded by $dZ_{max}$. The V-weighting compensates for convolving dispersed rays in each oblique planar projection. It is to be appreciated that for oblique planar projections, dZ and $dZ_{max}$ are larger than for oblique surface projections due to the larger dispersion factor. A three-dimensional backprojection is applied 455 to the sets of projections with the Z interpolation of the projections corresponding to a linear position in V along the oblique planar image matrix. A rectangular (x,y,z) volumetric data set is generated 460 by interpolating the oblique surface matrices along the z-direction. It should be appreciated that the sequence of reconstructions along the z-axis is separated by no more that the half-width of a single radiation detector. The resulting volumetric data set is filtered 465 along the z-direction to define the effective z-axis resolution.

Figure 4E:
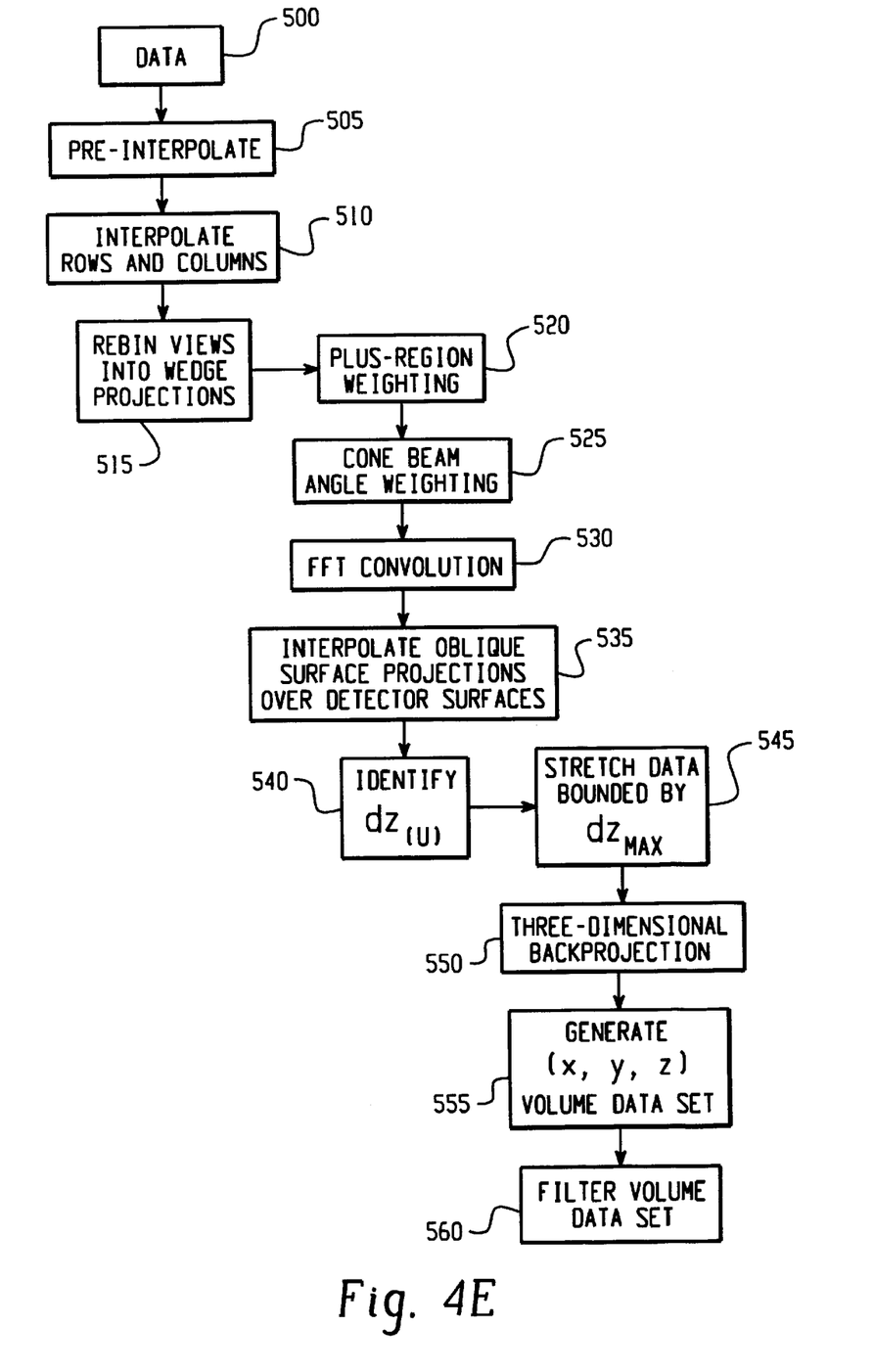

FIG. 4E illustrates an alternate embodiment which is analogous to the embodiment illustrated in FIG. 4C where views are rebinned into wedge projections. More particularly, data is collected 500 in the native sampling geometry, such as flat, source arc, or scan center arc. Columns and rows are pre-interpolated 505 or up-sampled by a factor of two using high-order interpolation. Optionally, the first and last rows are duplicated, if necessary. Alternately, for embodiments in which the number of rows is small, the 180° data points from the first row are used to interpolate the points at the end of the last row. The row and column elements are interpolated 510 to generate equiangular data which is orthogonal to the z-axis with the rows and partial rows equally spaced along the z-axis. The views are rebinned 515 in both the azimuthal and radial directions into wedge projections.

Following rebinning 515, a plus-region weighting algorithm is applied 520 along $Z(\theta)$ based on 180° oblique surface projections and end projections. In order to account for the angular distribution of backprojected rays, a cone beam angle weighting algorithm 525 is applied. Elements in each row have the same cosine weight value because the rows are equally distributed along the z-axis. After the projections along rows are completed, a FFT convolution 530 is performed on all of the rows. Following the convolution, the oblique surface projections are interpolated 535 over each detector surface into oblique surface projection rows and columns.

Following the interpolation, dZ(U) required to backproject onto a surface at $z=z_0$ is identified 540 around each oblique surface. The samples are interpolated to stretch the data 545 along U bounded by dZ(U) to projections bounded by $dZ_{max}$. A three-dimensional backprojection is applied 550 to the sets of projections with the Z interpolation of the projections corresponding to a linear position in V along the oblique surface image matrix. A rectangular (x,y,z) volumetric data set is generated 555 by interpolating the oblique surface matrices along the z-direction. It should be appreciated that the sequence of reconstructions along the z-axis is separated by no more that the half-width of a single radiation detector. The resulting volumetric data set is filtered 560 along the z-direction to define the effective z-axis resolution.

Figure 4F:
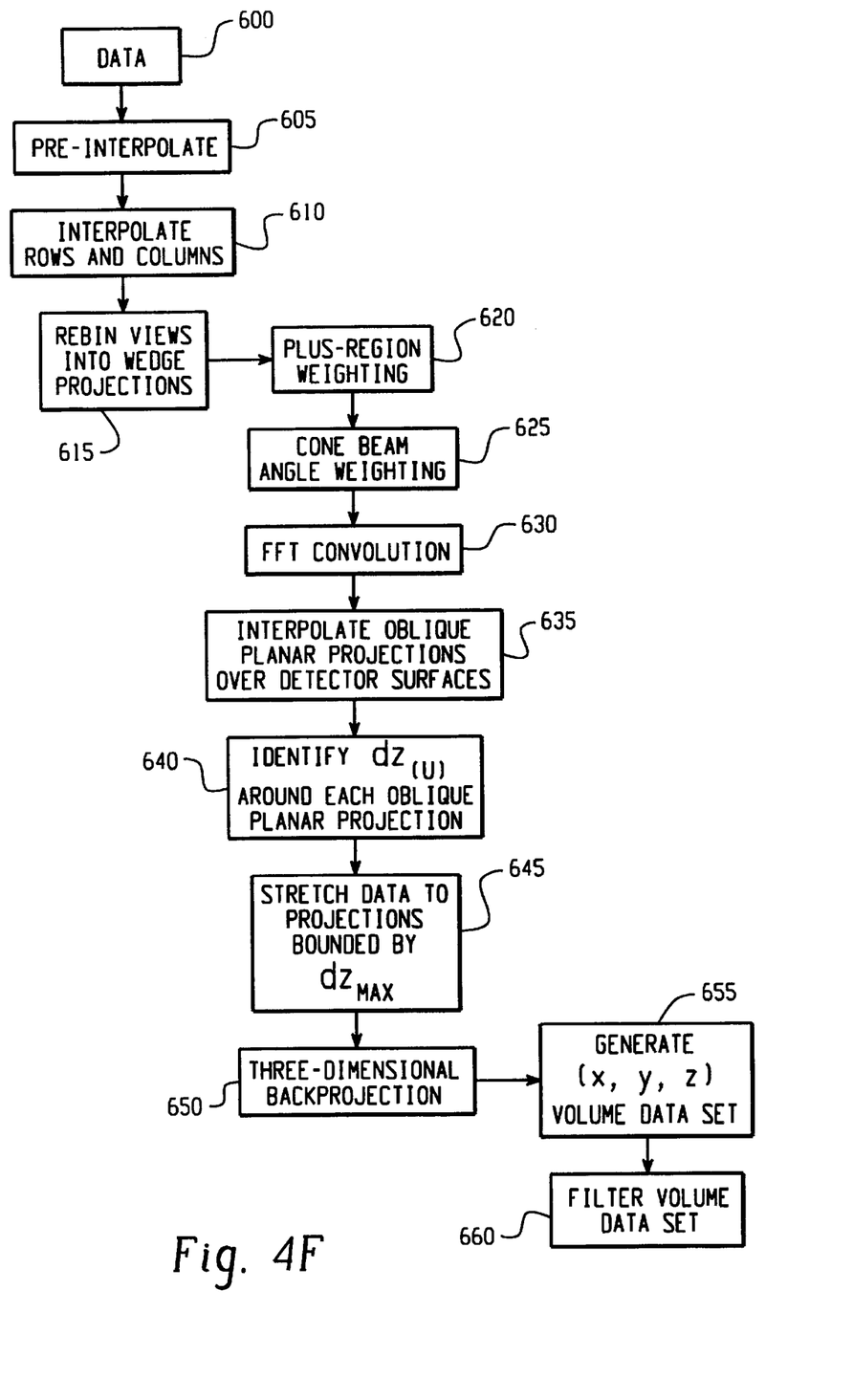

FIG. 4F illustrates aln alternate embodiment which is analogous to the embodiment illustrated in FIG. 4E where the oblique surfaces are defined as planar surfaces. More particularly, data is collected 600 in the native sampling geometry, such as flat, source arc, or scan center arc. Columns and rows are pre-interpolated 605 or up-sampled by a factor of two using high-order interpolation. Optionally, the first and last rows are duplicated, if necessary. Alternately, for embodiments in which the number of rows is small, the 180° data points from the first row are used to interpolate the points at the end of the last row. The row and column elements are interpolated 610 to generate equiangular data which is orthogonal to the z-axis with the rows and partial rows equally spaced along the z-axis. The views are rebinned 615 in both the azimuthal and radial directions into wedge projections.

Following rebinning 615, a plus-region weighting algorithm is applied 620 along $Z(\theta)$ based on 180° oblique surface projections and end projections. In order to account for the angular distribution of backprojected rays, a cone beam angle weighting algorithm 625 is applied. Elements in each row have the same cosine weight value because the rows are equally distributed along the z-axis. After the projections along rows are completed, a FFT convolution 630 is performed on all of the rows. Following the convolution, the oblique planar projections are interpolated 635 over each detector surface into oblique surface projection rows and columns.

Following the interpolation, the dZ(U) required to backproject onto the plane at $z=z_0$ is identified 640 around each oblique planar projection. It should be appreciated that for oblique planar projections dZ and $dZ_{max}$ are larger than for oblique surface projections due to the larger dispersion factor. The samples are interpolated to stretch the data 645 along U bounded by dZ(U) to projections bounded by $dZ_{max}$. A three-dimensional backprojection is applied 650 to the sets of projections with the Z interpolation of the projections corresponding to a linear position in V along the oblique planar image matrix. A rectangular (x,y,z) volumetric data set is generated 655 by interpolating the oblique surface matrices along the z-direction. It should be appreciated that the sequence of reconstructions along the z-axis is separated by no more that the half-width of a single radiation detector. The resulting volumetric data set is filtered 660 along the z-direction to define the effective z-axis resolution.

It should be appreciated that the oblique surface derivation is the same for embodiments where two-dimensional convolution and backprojection algorithms are applied as for embodiments where corresponding three-dimensional reconstruction algorithms are applied. Further, applying a three-dimensional backprojection algorithm to the defined surfaces provides greater accuracy and requires a minimal set of projections for complete image reconstruction.

The invention has been described with reference to the preferred embodiment. Modifications and alterations will occur to others upon a reading and understanding of the preceding detailed description. It is intended that the invention be construed as including all such modifications and alterations insofar as they come within the scope of the appended claims or the equivalents thereof.

Having thus described the preferred embodiments, the invention is now claimed to be:

1. A method of volumetric image reconstruction from partial cone beam data comprising:
    (a) collecting the partial cone beam data in two-dimensional arrays at a plurality of sampling positions, said collected data corresponding to rays of radiation diverging in two dimensions from a common vertex as the vertex travels along a continuous path;
    (b) identifying rays of radiation which pass through each of a plurality of oblique surfaces in a region of interest;
    (c) reconstructing data from the identified rays into a reconstruction cylinder having an axis along a z-direction; and
    (d) generating a volume data set from the reconstructed oblique surface data.

2. The method according to claim 1 further comprising:
    rebinning the collected data into a wedge beam format, wherein sets of parallel rays are grouped to define planes of radiation that angularly diverge from a common axis.

3. The method according to claim 1, wherein step (b) includes:
    at each sampling position, identifying non-redundant rays of radiation traversing each oblique surface throughout the region of interest.

4. The method according to claim 1, wherein step (b) includes:
    at each sampling position, identifying rays off penetrating radiation that intersect at a center point of each oblique surface.

5. The method according to claim 4, wherein step (b) further includes:
    identifying pixels on the oblique surface at least one pixel out from the center point, said pixels at least one pixel out from the center point forming a first surface ring; and
    identifying rays of penetrating radiation which are tangent to the first surface ring.

6. The method according to claim 5, wherein the step (b) further includes;
    iteratively identifying pixels outward from the center point of each oblique surface to a reconstruction cylinder radius, said pixels forming a plurality of oblique surface rings; and
    iteratively identifying rays of penetrating radiation tangent to the surface rings.

7. The method according to claim 6, wherein step (b) includes interpolating closest adjacent rays between the center point and the reconstruction cylinder radius where partial cone beam data is not collected.

8. The method according to claim 7, wherein step (b) further includes weighting the interpolated rays by a weighting function such that the weights of opposing rays sum to unity.

9. The method according to claim 8, wherein weighting the interpolated rays includes:
    applying plus-region weighting along the z-direction; and
    applying cone beam angle weighting.

10. The method according to claim 9, wherein the vertex travels along a helical path.

11. The method according to claim 10, wherein step (c) includes:
    computing a two-dimensional convolution of the weighted data; and two-dimensionally backprojecting the weighted convolution into a volumetric image memory.

12. The method according to claim 1, said method further comprising:
    defining a plurality of path segments along the path of the vertex, said path segments being at least 180° plus a fan angle of the cone beam; and,
    in step (b), each of the oblique surfaces is derived from the corresponding path segment.

13. The method according to claim 12, wherein the vertex travels along a helical path.

14. The method according to claim 7, wherein the spacing of the reconstructed surfaces along the longitudinal axis of the reconstruction cylinder is not greater than one-half of an effective longitudinal axis resolution.

15. The method according to claim 1, wherein step (d) includes:
    interpolating matrices corresponding to the reconstructed oblique surface data along the longitudinal direction to form the volume data set; and
    filtering the resulting volume data set along the longitudinal direction in order to define an effective longitudinal axis resolution.

16. A method of radiographic diagnostic imaging comprising:
    (a) generating penetrating radiation;
    (b) receiving the penetrating radiation with two-dimensional radiation detectors along a plurality of divergent rays, the rays being focused at a common origin vertex and diverging in two dimensions;
    (c) rotating the vertex along at least an arc segment of a helical path;
    (d) sampling the radiation detectors at a plurality of angular increments along the helical arc segment to generate a plurality of two-dimensional projection views, each view including a two-dimensional array of data values, each data value corresponding to one of the divergent rays;

(e) defining a first and a last oblique surface formed by the intersection of a cone beam of penetrating radiation and a region of interest;

(f) defining a plurality of additional oblique surfaces, said plurality of oblique surfaces being at least one of rotated and translated with respect to the first oblique surface;

(g) weighting projection views corresponding to each oblique surface;

(h) computing a convolution of the projection view data; and (i) backprojecting the convolved projection data corresponding to each oblique surface into a volumetric image memory.

17. The method according to claim 16, wherein steps (e) and (f) include:

identifying the rays of penetrating radiation that intersect at a center point of the oblique surface;

iteratively identifying pixels outward from the center point to an outward radius of a reconstruction cylinder, said outward pixels forming a plurality of oblique surface rings; and iteratively identifying rays of penetrating radiation which are tangent to each of the plurality of oblique surface rings.

18. The method according to claim 17, wherein steps (e) and (f) further include:

interpolating closest adjacent rays tangent to the oblique surface rings between the center point and the outer radius of the reconstruction cylinder where penetrating radiation was not detected.

19. A method of selecting non-redundant rays of penetrating radiation during a computed tomography scan, said non-redundant rays forming a plurality of oblique surfaces for reconstruction into a volumetric image representation, said method comprising:

at each angular orientation about an examination region, selecting detected rays of penetrating radiation that intersect a geometric center point of each oblique surface; and iteratively identifying rays of penetrating radiation which are tangent to surface rings extending outward from the geometric center point of each oblique surface.

20. The method according to claim 19, said method further comprising:

where penetrating radiation data does not exists, interpolating closest adjacent rays tangent to the oblique surface rings between the center point and an outer radius of region of interest.

21. The method according to claim 20, wherein each oblique surface is at least one of translated and rotated with respect to a first oblique surface.

22. A computed tomography (CT) scanner comprising:

a first gantry which defines an examination region;

a rotating gantry mounted on the first gantry for rotation about the examination region;

a source of penetrating radiation arranged on the rotating gantry for rotation therewith, said source of penetrating radiation emitting a cone-shaped beam of radiation that passes through the examination region as the rotating gantry rotates;

a subject support which holds a subject being examined at least partially within the examination region, wherein at least one of the first gantry and the subject support is translated such that the subject passes through the examination region while the rotating gantry is rotated and the source of penetrating radiation follows a helical path relative to the subject;

a two-dimensional array of radiation detectors arranged to receive the radiation emitted from the source of penetrating radiation after it has traversed the examination region;

a reconstruction processor which reconstructs images of the subject from data collected by the two-dimensional array of radiation detectors, said reconstruction processor including:

a control processor which defines a plurality of oblique surfaces, said oblique surfaces being defined by the intersection of the cone-shaped beam of radiation and a portion of the subject;

an interpolator which identifies non-redundant rays of penetrating radiation that pass through the oblique surfaces;

a first data processor which weights the data corresponding to the identified non-redundant rays;

a second data processor which receives the data from the first data processor and performs a convolution on the data; and, a backprojector which receives the data from the second data processor and backprojects it into an image memory; and, a human-viewable display which accesses the image memory to display reconstructed images of the subject.

23. The CT scanner according to claim 22, wherein the first data processor applies (i) plus region weighting, and (ii) cone beam angle weighting to the data.

24. The CT scanner according to claim 22, wherein the interpolator:

at each sampling position, identifies rays of penetration radiation that intersect at a center point of each oblique surface;

iteratively identifies pixels outward from the center point of each oblique surface to an outward radius of a reconstruction cylinder, said outward pixels forming a plurality of oblique surface rings; and, iteratively identifies rays of penetrating radiation which are tangent to each of the plurality of oblique surface rings.

25. The CT scanner according to claim 23, wherein the interpolator interpolates nearest adjacent rays which are tangent to the oblique surface rings.

26. The method according to claim 16 wherein:

convolution of the backprojection view data is computed one of two-dimensionally and three-dimensionally; and, the convolved projection data is backprojected one of two-dimensionally and three-dimensionally.

27. The apparatus according to claim 22 wherein:

the second data processor performs one of a two-dimensional and three-dimensional convolution on the data; and the backprojector backprojects the data received from the second data processor one of two-dimensionally and three-dimensionally into the image memory.

28. A method of image reconstruction from partial cone beam data comprising:

(a) collecting the partial cone beam data in two-dimensional arrays at a plurality of sampling positions, said collected data corresponding to rays of radiation diverging in two dimensions from a common vertex as the vertex travels along a continuous path;

(b) defining a plurality of oblique surfaces throughout a region of interest;

(c) identifying rays of radiation which pass through the plurality of oblique surfaces;

(d) reconstructing data from the identified rays into a reconstruction cylinder having an axis along a z-direction, said recomstructing including:
computing a three-dimensional convolution of the data; and,
three-dimensionally backprojecting the convolution into a volumetric image memory; and, (e) generating a volume data set from the reconstructed oblique surface data.

29. A radiographic diagnostic imaging apparatus comprising:

(a) a means for generating penetrating radiation;

(b) a two-dimensional array of radiation detectors for receiving the penetrating radiation along a plurality of divergent rays, the rays being focused at a common origin vertex and diverging in two dimensions;

(c) a means for rotating the vertex along at least an arc segment of a helical path;

(d) a means for sampling the radiation detectors at a plurality of angular increments along the helical arc segment to generate a plurality of two-dimensional projection views, each view including a two-dimensional array of data values, each data value corresponding to one of the divergent rays;

(e) a means for defining a first and a last oblique surface formed by the intersection of a cone beam of penetrating radiation and a region of interest;

(f) a means for defining a plurality of additional oblique surfaces, said plurality of oblique surfaces being at least one of rotated and translated with respect to the first oblique surface;

(g) a means for weighting projection views corresponding to each oblique surface;

(h) a means for computing a convolution of the projection view data; and (i) a means for backprojecting the convolved projection data corresponding to each oblique surface into a volumetric image memory.

* * * * *